United States Patent [19]

Lancaster et al.

[11] Patent Number: 5,445,795
[45] Date of Patent: Aug. 29, 1995

[54] VOLATILE ORGANIC COMPOUND SENSING DEVICES

[75] Inventors: Gregory D. Lancaster; Glenn A. Moore; Mark L. Stone, all of Idaho Falls, Id.; William K. Reagen, Stillwater, Minn.

[73] Assignee: The United States of America as represented by the United States Department of Energy, Washington, D.C.

[21] Appl. No.: 153,448

[22] Filed: Nov. 17, 1993

[51] Int. Cl.6 .......................... G01N 21/01; G01J 1/48
[52] U.S. Cl. .................................. 422/86; 422/82.05;
422/82.06; 422/82.09; 422/82.11; 422/87; 422/91
[58] Field of Search ................ 123/519; 422/59, 60, 422/82.05, 82.06, 82.09, 82.11, 86–88, 91

[56] References Cited

U.S. PATENT DOCUMENTS

| | | | |
|---|---|---|---|
| Re. 31,879 | 5/1985 | Lübbers et al. | 422/59 X |
| 4,032,297 | 6/1977 | Lyshkow | 422/91 |
| 4,159,304 | 6/1979 | Shono | 422/59 X |
| 4,245,997 | 1/1981 | Wiesner | 422/59 X |
| 4,668,635 | 5/1987 | Forster | 422/91 X |
| 4,752,447 | 6/1988 | Kimmel et al. | 422/56 |
| 4,782,234 | 11/1988 | Chudyk et al. | 250/372 |
| 4,826,774 | 5/1989 | Nagel | 436/106 |
| 4,846,548 | 7/1989 | Klainer | 350/96.29 |
| 4,863,694 | 9/1989 | Kimmet et al. | 422/91 X |
| 4,892,383 | 1/1990 | Klainer et al. | 350/96.29 |
| 4,897,551 | 1/1990 | Gersh et al. | 250/301 X |
| 4,913,881 | 4/1990 | Evers | 422/91 X |
| 4,963,324 | 10/1990 | May | 422/60 |
| 4,973,561 | 11/1990 | Hansen et al. | 422/81 X |
| 5,010,776 | 4/1991 | Lucero et al. | 73/863.23 |
| 5,039,491 | 8/1991 | Saaski et al. | 422/82.05 |
| 5,157,261 | 10/1992 | Grey et al. | 250/458.1 |
| 5,186,153 | 2/1993 | Steinbrenner et al. | 123/519 |
| 5,244,813 | 9/1993 | Walt et al. | 436/172 |

FOREIGN PATENT DOCUMENTS

| | | |
|---|---|---|
| 391759 | 5/1990 | Austria . |
| 3908936 | 9/1990 | Germany . |
| 1545572 | 5/1979 | United Kingdom . |

OTHER PUBLICATIONS

S. M. Inman et al. *Anal. Chim. Acta.* 1990, 239, 45–51.
R. J. Berman et al. *Anal. Chem.* 1990, 62, 2066–2071.
C. Zhu et al. *Anal. Chem.* 1990, 62, 2079–2084.
S. H. Lieberman et al. *Chem. Abstr.* 1991, 114, 198618w.
"Portable Vapochromatic/Fiber Optic Detector for VOCs in Air and Water", Ames Laboratory, Technical Data Sheet, Nov. 17–19, 1992, pp. 1–2.

Primary Examiner—James C. Housel
Assistant Examiner—Arlen Soderquist
Attorney, Agent, or Firm—Tim Harney; Hugh Glenn; William R. Moser

[57] ABSTRACT

Apparatus employing vapochromic materials in the form of inorganic double complex salts which change color reversibly when exposed to volatile organic compound (VOC) vapors is adapted for VOC vapor detection, VOC aqueous matrix detection, and selective VOC vapor detection. The basic VOC vapochromic sensor is incorporated in various devices such as a ground probe sensor, a wristband sensor, a periodic sampling monitor, a soil/water penetrometer, an evaporative purge sensor, and various vacuum-based sensors which are particularly adapted for reversible/reusable detection, remote detection, continuous monitoring, or rapid screening of environmental remediation and waste management sites. The vapochromic sensor is used in combination with various fiber optic arrangements to provide a calibrated qualitative and/or quantitative indication of the presence of VOCs.

15 Claims, 11 Drawing Sheets

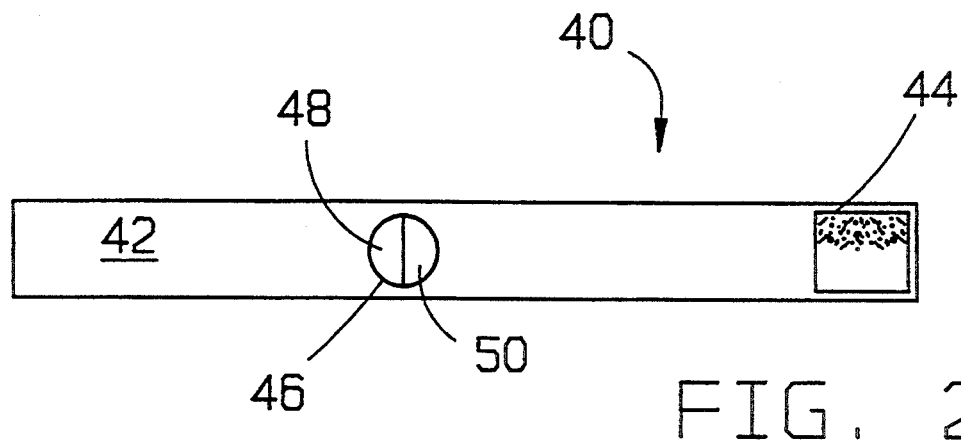
FIG. 2
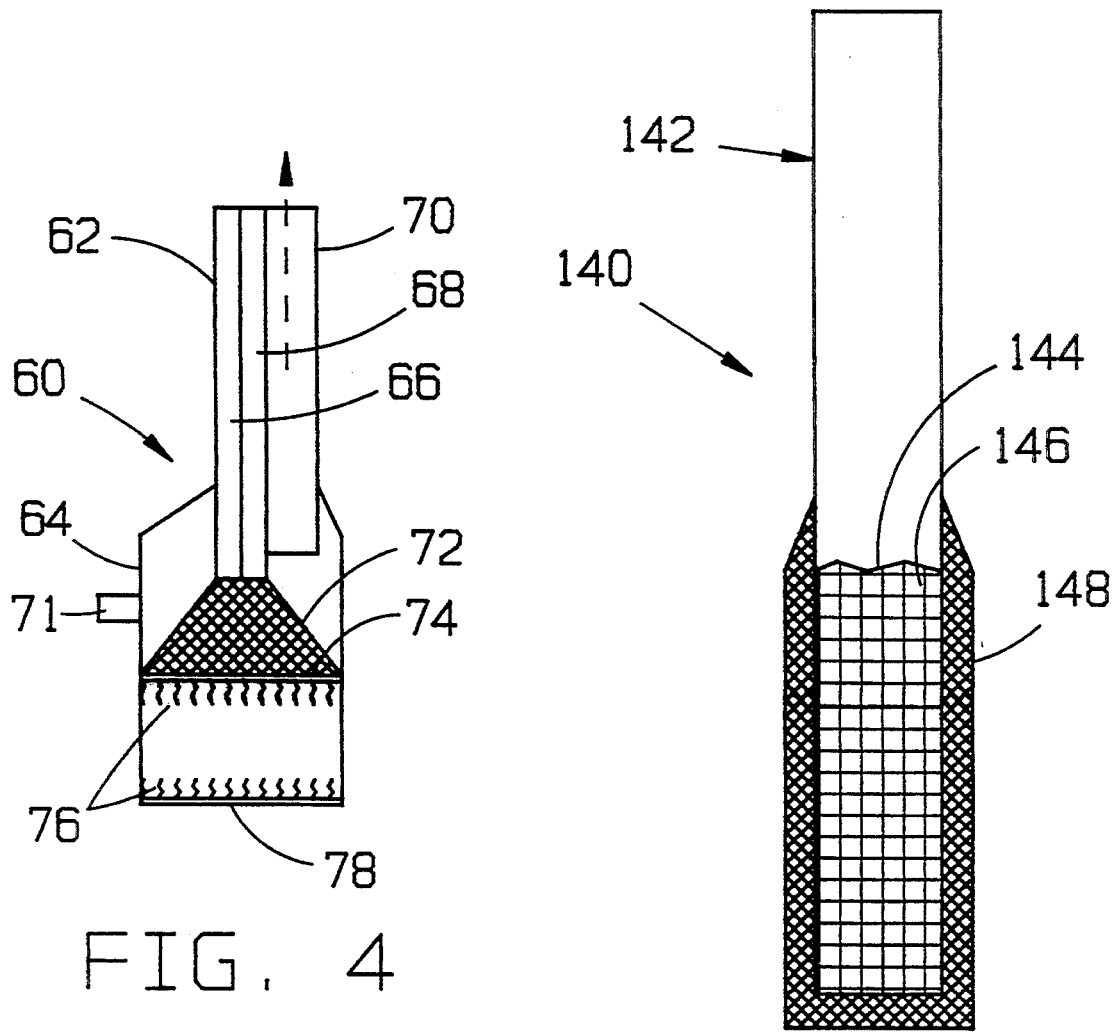
FIG. 4
FIG. 6

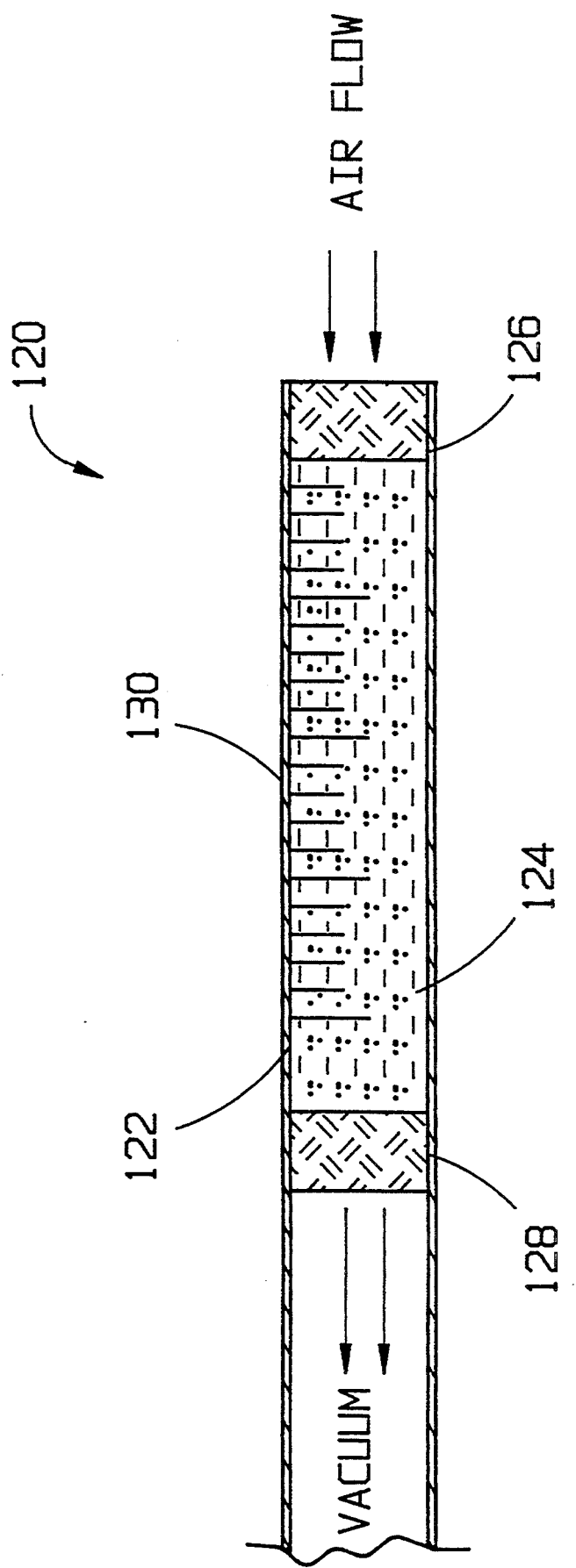

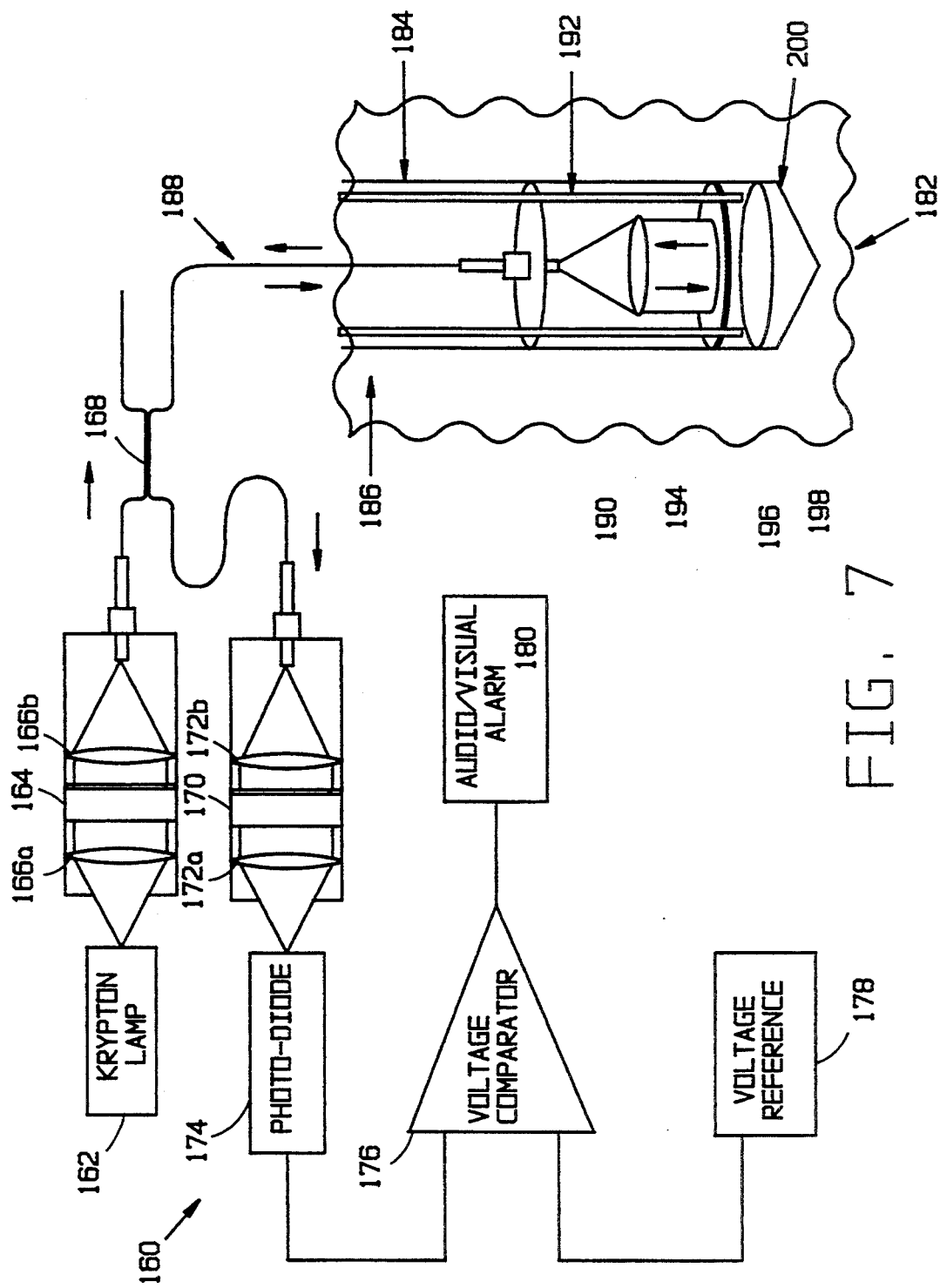

VOLATILE ORGANIC COMPOUND SENSING DEVICES

CONTRACTUAL ORIGIN OF THE INVENTION

The United States Government has rights in this invention pursuant to Contract No. DE-AC07-76ID01570 between the U.S. Department of Energy and Idaho National Engineering Laboratory.

FIELD OF THE INVENTION

This invention relates generally to the optical detection of chemical species and is particularly directed to apparatus for detection of volatile organic compounds (VOCs), VOC aqueous matrix detection, and selective VOC vapor detection.

BACKGROUND OF THE INVENTION

Pollution detection and monitoring has become of utmost importance as environmental issues and the protection and preservation of natural resources has greatly increased in the public awareness. Substantial technical advances have been made in environmental monitoring and control systems. Such systems should be highly sensitive and responsive to minute quantities of a contaminant and should furthermore be capable of identifying a particular contaminant. Moreover, it is highly desirable that such systems be low in cost, easy to use and adapted for use in remote or inaccessible locations.

One of the more common pollutants is volatile organic compounds (VOCs). A common example of contamination of groundwater is from leaks in underground storage tanks used for storing VOCs such as gasoline and other liquid petroleum fuels. Other VOCs such as organic solvents and lubricants are commonly disposed of at hazardous waste sites such as landfills and often find their way as contaminants to groundwater. Early detection of such contaminants would obviously be highly desirable to minimize damage and facilitate restoration of the environment. Selective identification of a particular VOC would also be highly desirable because it could assist in identifying the source of contamination.

Transition metal-containing double complex salts exhibiting "vapochromism, i.e. a change in color or absorbance in the electromagnetic spectrum, such as in the visible portion of the spectrum, induced by vapors of organic compounds having a designated vapor pressure at room temperature, are disclosed in U.S. Pat. No. 4,826,774. These vapochromic compounds undergo reversible color and fluorescence changes in the absence and presence of VOCs. These types of vapor detecting materials have not yet been incorporated in detection devices which are capable of practical use.

U.S. Pat. No. 5,244,813 discloses another approach to detecting organic analytes involving the absorption and partitioning of the analytes for optical determination which makes use of fiber optic sensors utilizing polarity sensitive solvachromic dyes and polymeric materials. U.S. Pat. Nos. 4,846,548 and 4,892,383 disclose fiber optic chemical sensors (FOCS) for detecting the presence of chemical or biological species by measuring changes in the total internal reflection characteristics of the fiber optic element produced by changes in the index of refraction of a clad or layer of a material which reacts with the chemical or biological species. The latter patent discloses a specific embodiment incorporating a reservoir FOCS formed of a modular cell body. U.S. Pat. No. 5,010,776 discloses an environment contamination detection and analyzing system, such as for use with subsurface contaminants, which includes a probe which collects a fluid sample from the medium for determining the presence of a contaminant having a vapor pressure. Pneumatic communication lines are connected to the probe for transporting a fluid sample by a carrier gas to a detector/analyzer for analysis of the contaminant. None of the aforementioned approaches are adapted for the aqueous media detection of VOCs or the selective detection of VOCs in a low cost device which is easily transported.

The present invention addresses the aforementioned limitations of the prior art by providing apparatus for the optical detection of chemical species such as VOCs, VOC aqueous matrix detection, and selective VOC vapor detection.

OBJECTS AND SUMMARY OF THE INVENTION

Accordingly, it is an object of the present invention to provide for the reversible/reusable detection of VOCs using vapochromic materials in combination with fiber optics.

It is another object of the present invention to provide various arrangements for the optical detection of VOCs which are reusable, low in cost, have a rapid response time and are particularly adapted for remote detection, continuous monitoring and/or rapid screening of VOCs such as in waste management and treatment and site environmental restoration.

Yet another object of the present invention is to provide a portable, self-contained apparatus for the detection of VOCs in either vapor form or in an aqueous media which is useful in environmental screening and monitoring of air, water and soils such as in air sampling, sniffing for leaking drums, and groundwater sampling.

These objects of the present invention are achieved and the disadvantages of the prior art are eliminated by an apparatus for detecting volatile organic compounds (VOCs) comprising: a vapochromic sensor responsive to the presence of a VOC, wherein the vapochromic sensor undergoes a color change when in contact with a VOC; a sensor chamber containing the vapochromic sensor; a light source coupled to the sensor chamber for providing a reference light beam and for directing the reference light beam into the sensor chamber and onto the vapochromic sensor; a light detector coupled to the sensor chamber and responsive to light reflected from the vapochromic sensor; and a detection arrangement coupled to the light source and to the light detector for comparing the reference light beam and the light reflected from the vapochromic sensor for determining a color change in the vapochromic sensor arising from the presence of VOCs.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

FIG. 1A is an enlarged view of the sensor head of the VOC ground probe sensor of FIG. 1.

FIG. 2 is a simplified schematic diagram of a VOC chemical sensor in the form of a wristband in accordance with another embodiment of the present invention;

FIG. 4 is a simplified sectional view of a VOC vapochromic sensor in accordance with another aspect of the present invention;

FIG. 5 is a simplified schematic diagram of another embodiment of a VOC vapochromic sensor in accordance with the present invention;

FIG. 6 is a simplified schematic diagram of yet another embodiment of a VOC vapochromic sensor in accordance with the principles of the present invention;

FIG. 7 is a soil/water penetrometer in accordance with another aspect of the present invention;

DETAILED DESCRIPTION OF THE PREFERRED EMBODIMENTS

Figure 1:
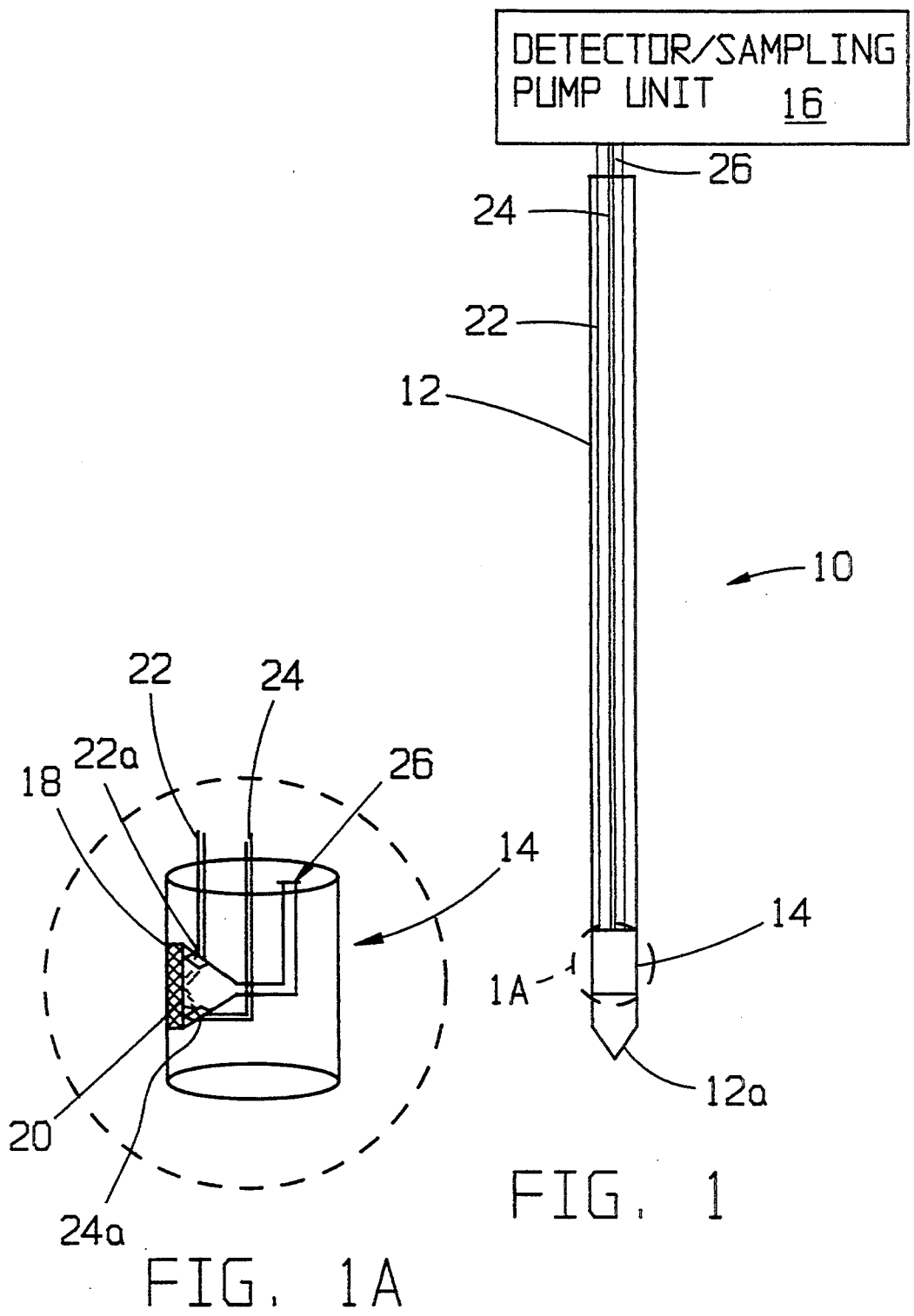
FIG. 1 is a simplified schematic diagram of a VOC ground probe sensor in accordance with one embodiment of the present invention.

Referring to FIG. 1, there is shown a simplified schematic diagram of a ground probe 10 for detecting subsurface volatile organic compounds (VOCs) in accordance with one embodiment of the present invention. Ground probe 10 includes an elongated, linear, rigid shaft 12 having a tapered distal end 12a. Shaft 12 is adapted for insertion in the soil to measure the VOC content. Disposed adjacent the distal end 12a of shaft 12 is a sensor head 14. An enlarged view of the sensor head 14 is shown in FIG. 1A and is described in the following paragraphs.

Sensor head 14 includes a generally cylindrical housing having a porous sampling window 18 in a lateral portion thereof. Disposed on the inner surface of the porous sampling window 18 is a vapochromic chemical sensor coating 20. The porous sampling window 18 allows any VOCs in the soil to contact the vapochromic chemical sensor coating 20 causing it to change color. Disposed within shaft 12 and coupling a detector/sampling pump unit 16 to the sensor head 14 are first and second optical fibers 22 and 24 having respective ends 22a and 24a. An optical output signal is provided from the detector/sampling pump unit 16 to the first optical fiber 22 where it exits end 22a of the optical fiber and is incident on the vapochromic chemical sensor coating 20. Light is reflected from the chemical sensor coating 20 onto the end 24a of the second optical fiber 24, with the reflected light provided to the detector/sampling pump unit 16 for determining the extent of color change of the chemical sensor coating representing the amount; of VOCs which have passed through the porous sampling window 18 and contacted the chemical sensor coating. Also disposed within shaft 12 and coupling the detector/sampling pump unit 16 to the sensor head 14 is a vacuum line 26. The detector-sampling pump unit 16 evacuates the vacuum line 26 drawing air through the porous sampling window 18 and into the sensor head 14 allowing any VOCs present to be deposited upon the chemical sensor coating 20. The combination of the first and second optical fibers 22, 24 and the vapochromic chemical sensor coating 20 thus provides for the remote detection of VOCs at a subsurface location.

Referring to FIG. 2, there is shown a disposable wristband sensor 40 in accordance with another aspect of the present invention. The disposable wristband sensor 40 includes a flexible band 42 having an adhesive member 44 for securing the band to the wrist, or other convenient body member, of a user. Disposed on band 42 is a vapochromic sensor element 46. Disposed over a first half of the vapochromic sensor element 46 is a porous coating 48, while disposed over a second half of the vapochromic sensor element is a solid, or reference, coating 50. The portion of the vapochromic sensor element 46 disposed beneath the solid coating 50 provides a visual reference indication in the form of a first color of the vapochromic sensor element 46. Porous coating 48 allows VOCs access to the vapochromic sensor element 46 for changing its color and providing a visual indication of the presence of VOCs when compared with the portion of the sensor element disposed under solid coating 50.

Figure 3:
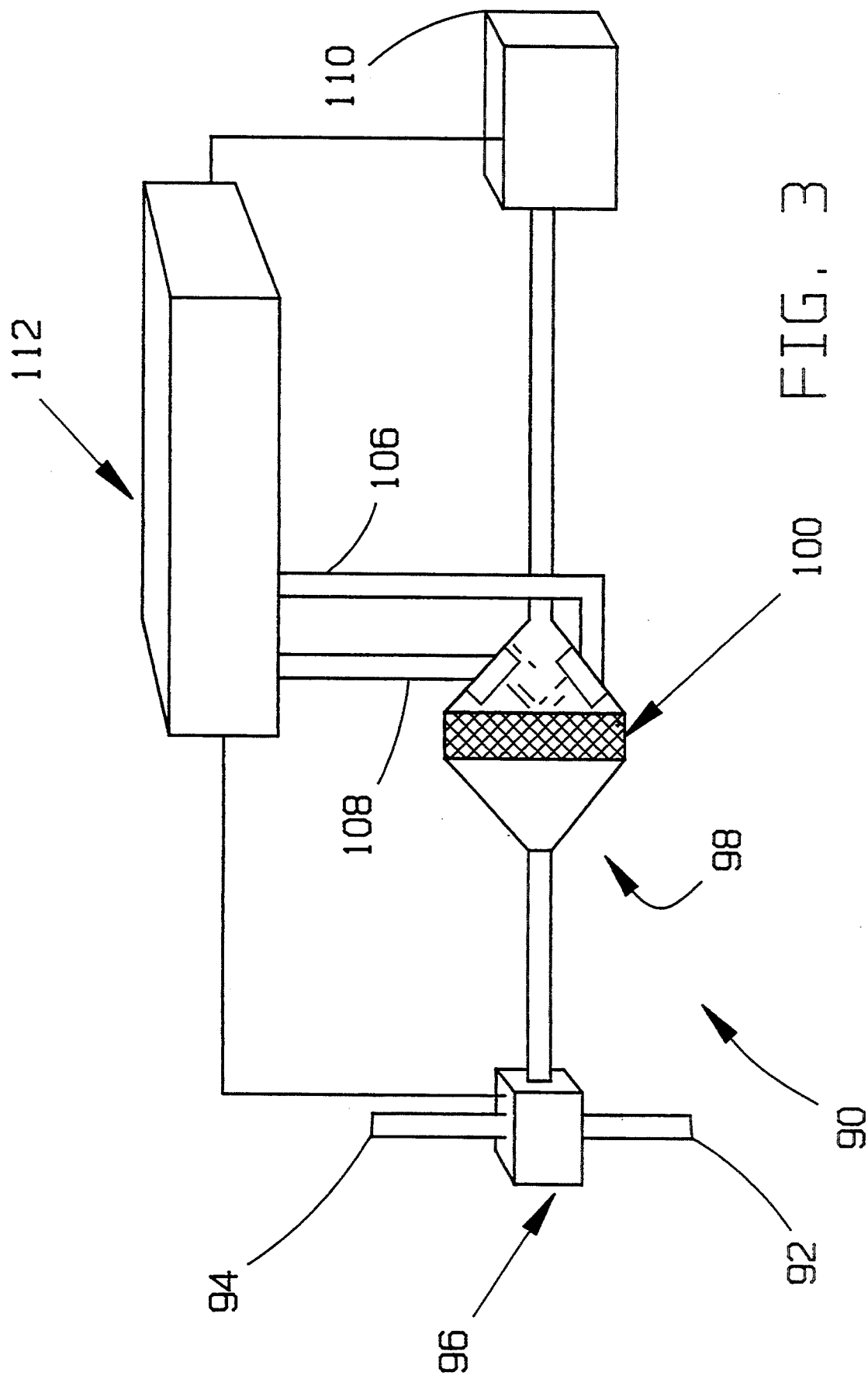
FIG. 3 is a simplified schematic and block diagram of a periodic sampling monitor in accordance with another aspect of the present invention.

Referring to FIG. 3, there is shown a combined simplified schematic and block diagram of a periodic sampling monitor 90 in accordance with another aspect of the present invention. Periodic sampling monitor 90 includes a VOC sampling port 92, a sensor purging port 94, and a two-way valve 96. Two-way valve 96 is coupled to a detector, data logger and closed loop sampling/purge controller 112. Controller 112 controls the two-way valve 96 for admitting either a VOC, if present, through sampling port 92 or uncontaminated air through purging port 94 for purging a sensor cell 98. Sensor cell 98 is coupled to the two-way valve 96 and includes a porous substrate and sensor material coating 100 and first and second optical fibers 106 and 108. The first and second optical fibers 106, 108 are coupled to controller 112 for directing light onto the sensor material coating 100 which is comprised of a vapochromic material. An indication of color changes in the sensor material coating 100 is provided via one of the optical fibers to controller 112 in providing an indication of the presence of VOCs. Also coupled to the detector, data logger and closed loop sampling/purge controller 112 as well as to the sensor cell 98 is a vacuum sampling pump 110. Vacuum sampling pump 110 is employed to draw increasing volumes of VOCs through the sensor cell 98 when VOC vapor has built-up within the sensor cell over time and increasingly higher concentrations of VOCs are required for detection. By switching the two-way valve 96 to the sensor purging port 94, clean air may be directed through the sensor cell 98 allowing it to return to its original state, or color. Operation of the two-way valve 96 is synchronized with the sampling rate of the detector, data logger and closed loop sampling/purge controller 112.

Referring to FIG. 4, there is shown a simplified sectional view of a VOC vapochromic sensor 60 in accordance with another aspect of the present invention. Vapochromic sensor 60 includes an elongated support/transmission member 62 and a sensor head 64. Disposed within the elongated support/transmission member 62 are a color detecting fiber 66, a light source fiber 68, and a vacuum line 70. Disposed within the sensor head 64 are a vapochromic material layer 74, a porous support member 76, and a VOC permeable, water impermeable membrane 78. The porous support member 76 separates and provides support for the vapochromic material layer 74 and the water impermeable membrane 78. Light source fiber 68 carries a light signal to the sensor head 64 which is directed onto the vapochromic material layer 74 and is shown in the form of a conical light beam 72. The light is reflected from the vapochromic material layer 74 to the color detecting fiber 66 which provides an indication of a color change undergone by the vapochromic material layer 74 in response to the presence of VOCs. Spacing adjustment means 71 (shown in the figure as a simple block) are provided between the light source fiber 68 and the vapochromic material layer 74 for adjusting the spacing between these two members. This allows for adjustment of the spacing between the light source fiber 68 and the vapochromic material layer 74 to optimize the amount of light incident upon the vapochromic material layer. This increases the light reflected from the vapochromic material layer 74 and facilitates detection of color changes in the vapochromic material layer, particularly in the case of small color changes.

Referring to FIG. 5, there is shown a longitudinal sectional view of another embodiment of a VOC vapochromic sensor 120 in accordance with the present invention. VOC vapochromic sensor 120 includes a cylindrical glass tube 122 having disposed therein in a spaced manner along the length thereof first and second plugs 126 and 128. First and second plugs 126, 128 are preferably comprised of a porous material such as cotton, glass frit or a polymeric material. Air is forced through the glass tube 120 and through the first and second porous plugs 126, 128 by forming a vacuum within the tube, whereupon air flow is in the direction of the arrows in the figure. Disposed intermediate the first and second plugs 126, 128 and within the glass tube 122 is a vapochromic material 124. Disposed in a spaced manner along the length of the glass tube 122 between the first and second plugs 126, 128 are a plurality of spaced calibration marks 130. As air flows through the glass tube 122 in the direction of the arrows, the presence of VOCs will cause the vapochromic material 124 to turn color progressively in a direction from right to left. The calibration marks 130 may be used to measure the extent, or length, of the vapochromic material 124 which has changed color to determine the amount or concentration of VOCs in the air flow.

Referring to FIG. 6, there is shown a simplified plan and sectional view of another embodiment of a vapochromic sensor 140 in accordance with the present invention. Vapochromic sensor 140 includes an optical fiber 142 shown in plan view in the upper portion of FIG. 6. The lower portion of the figure shows the optical fiber 142 in section as including an optical fiber core 144 from which the outer cladding layer has been removed such as by etching. The outer cladding layer of the optical fiber 142 has been replaced with a vapochromic material covering 146 which is disposed about the fiber's core 144. Disposed about the vapochromic material layer 146 is a VOC permeable, water impermeable membrane 148 which allows VOCs access to the vapochromic material layer 146, but prevents water from contacting the vapochromic material layer. Light from a source such as a photodiode (not shown in the figure for simplicity) is directed along the optical fiber 142 where it is incident upon and reflected by the vapochromic material layer 146. As the color of the vapochromic material layer 146 changes in the presence of VOCs, the light reflected back up the optical fiber 142 provides an indication of the extent of color change of the vapochromic material layer. A photodetector (also not shown in the figure for simplicity) coupled to the optical fiber 142 allows for the detection of the presence of VOCs and a determination of their concentration in the medium in which the vapochromic sensor 140 is disposed.

Referring to FIG. 7, there is shown a simplified schematic and block diagram of a soil/water penetrometer 160 in accordance with another aspect of the present invention. Penetrometer 160 includes a light source such as a krypton lamp 162 which directs a light beam into a filter and focusing arrangement comprised of a first band-pass filter 164 and first and second lenses 166a and 166b. A focused beam is directed into an optical fiber and thence to a fiber optic beam-splitter 168. Fiber optic beam-splitter 168 directs a portion of the beam via a fiber optic cable 188 to a sensor 182. Sensor 182 is enclosed within a penetrometer housing 184 having a tapered distal end. Sensor 182 includes an air/vacuum inlet 190, an air/vacuum outlet 192 and a collimating lens 194. Collimating lens 194 directs a collimated beam onto a vapochromic sensor coating 196 disposed within the sensor 182. The tapered distal end of housing 184 is provided with a perforated penetrometer section 200 to permit the passage of VOCs from contaminated water/soil 186 into the sensor 182. A VOC selective membrane 198 allows only VOCs to pass into the sensor 182, while preventing the entry of water and soil. A light signal representing the color of the vapochromic sensor coating 196 which, in turn, represents the concentration of VOCs within sensor cell 182 is provided via fiber optic cable 188 and beam-splitter 168 to the combination of a second band-pass filter 170 and third and fourth lenses 172a and 172b. The lens and filter combination provides an optical output to a photodiode 174 which, in turn, provides one input to a voltage comparator 176. Another input to the voltage comparator 176 is provided from a voltage reference 178, with the output of the voltage comparator provided to an audio/visual alarm 180 to provide an operator of the soil/water penetrometer 160 with an indication of the level of VOCs in the contaminated water/soil 186.

Figure 8:
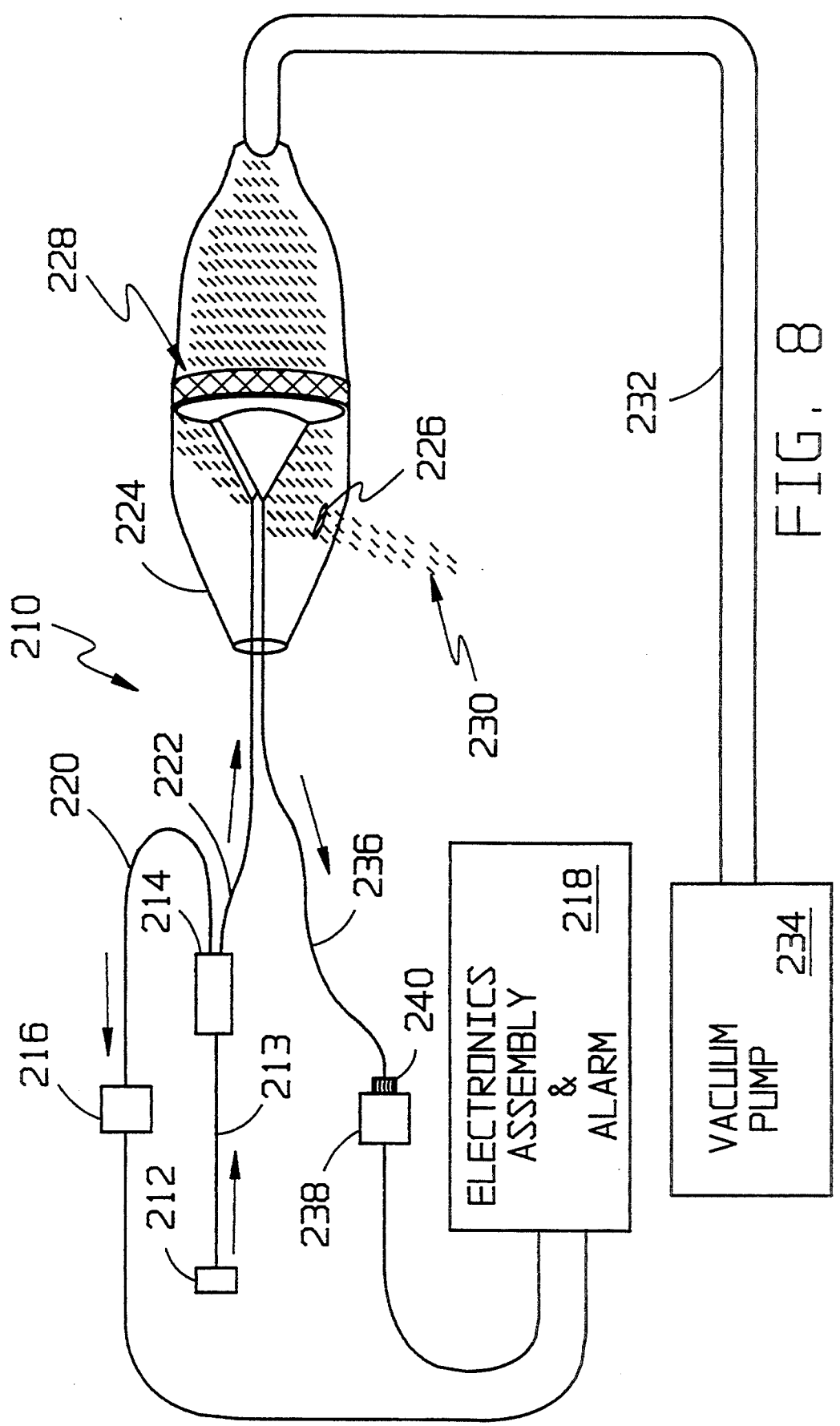
FIGS. 8 and 9 are simplified block and schematic diagrams of alternative embodiments of a volatile organic compound colorimetric sensor in accordance with another aspect of the present invention.

Referring to FIG. 8, there is shown a simplified combined block and schematic diagram of a VOC colorimetric sensor 210 in accordance with another aspect of the present invention. VOC colorimetric sensor 210 includes a light source 212 for directing a light signal via a first optical fiber 213 to a fiber optic beam-splitter 214. Beam-splitter 214 directs a first light signal via a second optical fiber 220 to a reference photodetector 216 and thence to an electronic assembly and alarm 218. Beam-splitter 214 also directs a second light signal via a third optical fiber 222 to a sensor chamber 224. Disposed within sensor chamber 224 is a vapochromic sensing element 228 through which is directed vapors 230 to be sampled. Vapors 230 are introduced into the sensor chamber 224 through a sampling port inlet 226 and are drawn through the sensor chamber by means of a vacuum pump 234 coupled to the sensor chamber via a vacuum line 232. Light incident upon the vapochromic sensing element 228 from the third optical fiber 222 is reflected back to a fourth optical fiber 236. The third and fourth optical fibers 222, 236 are placed side-by-side within the sensor chamber 224, with the cleaved ends approximately 0.25 inches from the vapochromic sensing element 228. Light from the third optical fiber 222 is allowed to diverge and is reflected from the vapochromic sensing element 228. Some of the reflected light enters the fourth optical fiber 236. The fourth optical fiber 236 is coupled to the combination of a "detect" photodetector 238 and an optical band-pass filter 240. The center wavelength of filter 240 is chosen to produce the largest change in measurement signal when the vapochromic sensing element 228 changes color indicating the presence of VOC vapors. The filtered optical signal is provided from the photodetector 238 to the electronics assembly and alarm 218 for processing. When VOC vapors are present in the sensor chamber 224, the vapochromic sensing element 228 changes color resulting in a change in the amount of the optical signal that passes through the optical band-pass filter 240 to photodetector 238. This reduction in optical signal results in a decreased electrical signal input to the electronics assembly and alarm system 218. An alarm will sound if the VOC concentration is great enough to cause a color change that produces a decreased optical signal and resulting electrical signal larger than a previously set alarm threshold.

Figure 9:
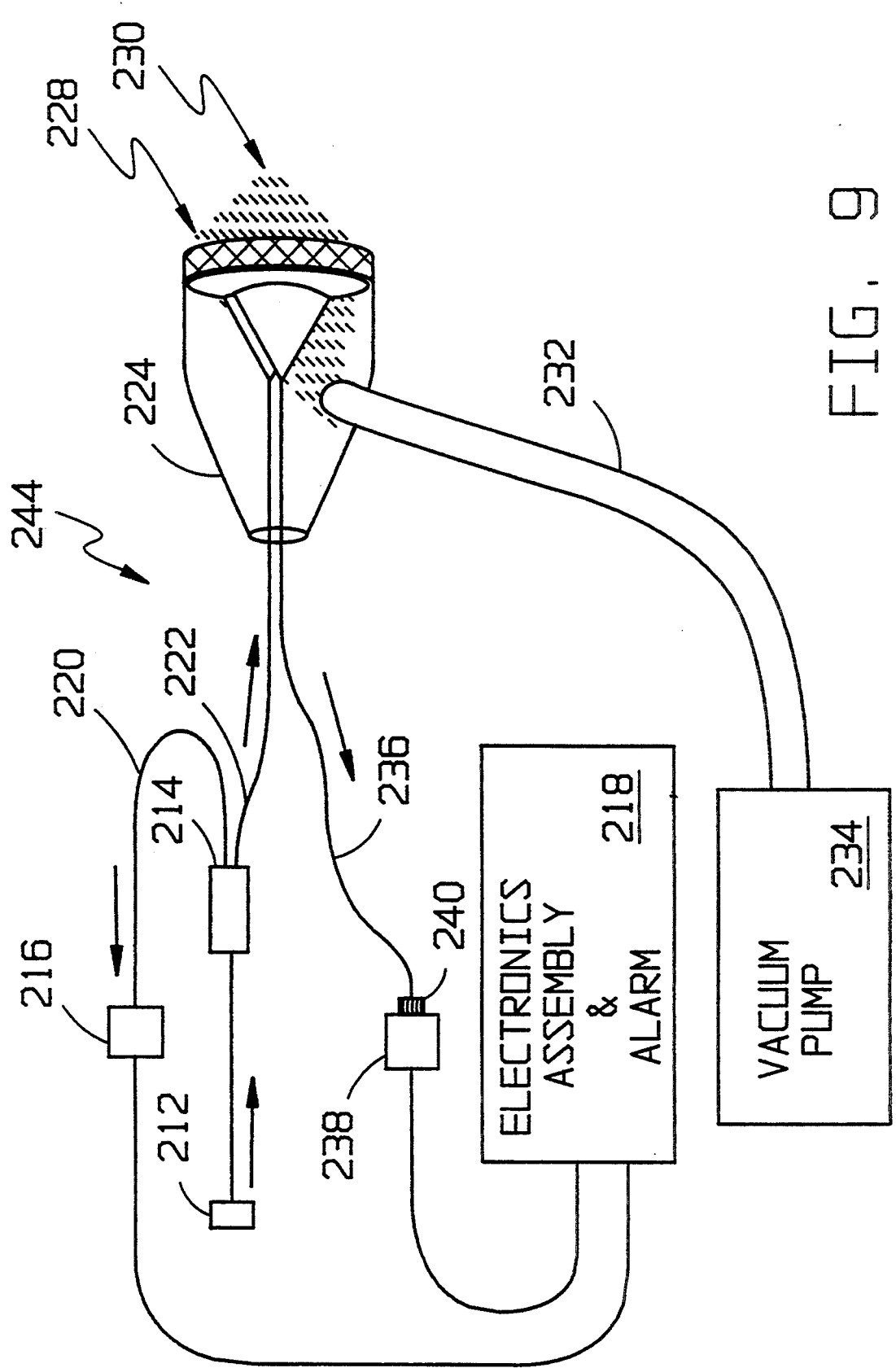

Referring to FIG. 9, there is shown another embodiment of a VOC colorimetric sensor 244 similar to that shown in FIG. 8. Common elements performing essentially the same function in the two VOC colorimetric sensors shown in FIGS. 8 and 9 are provided with the same identifying numbers. The difference in the VOC colorimetric sensor shown in FIG. 9 from that shown in FIG. 8 is that in the former embodiment the vacuum line 232 is coupled to the sensor chamber 224 on the opposite side of the vapochromic sensing element 228 from where the vapors 230 are introduced into the sensor chamber. This results in the vapors 230 to be sampled being drawn through the vapochromic sensing element 228 and into the sensor chamber 224 by the vacuum pump 234 via vacuum line 232. The sampling port inlet 226 in the embodiment of FIG. 8 is thus eliminated in the embodiment of FIG. 9 where the vapors 230 to be sampled are drawn into the sensor chamber 224 through the vapochromatic sensing element 228. In the embodiments of FIGS. 8 and 9, the vapochromic sensing element 228 is coated on a porous quartz frit.

Figure 10:
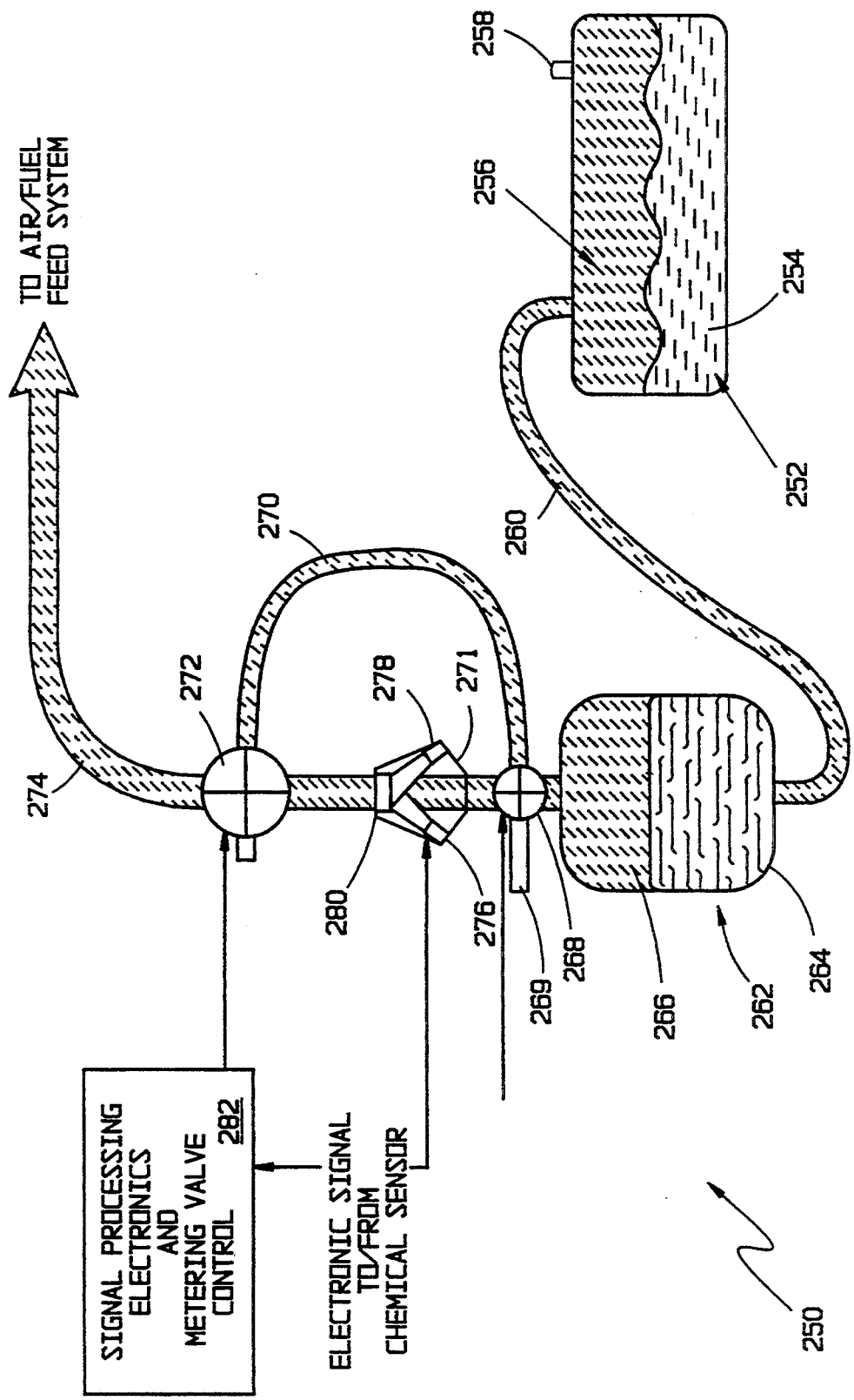
FIG. 10 is a simplified schematic diagram of an evaporative purge sensor in accordance with yet another aspect of the present invention.

Referring to FIG. 10, there is shown a simplified combined block and schematic diagram of an evaporative purge sensor 250 in accordance with another aspect of the present invention. The evaporative purge sensor 250 is intended for use in a vehicle containing a fuel tank 252 in which is disposed a liquid fuel 254 and fuel vapors 256. Fuel tank 252 includes an air vent 258 and is coupled to a carbon canister 262 by means of a first line 260. Carbon canister 262 includes a carbon filter 264 for absorbing fuel vapors emitted from fuel tank 252. When the carbon filter 264 becomes saturated, fuel vapors 266 collect in an upper portion of the carbon canister 262. Coupled to the carbon canister 262 is an inlet valve 268 which is also coupled to a clean air inlet 269 for purging a vapochromic sensor 280 also coupled to the inlet valve. The vapochromic sensor 280 is disposed together with a light emitting diode (LED) 276 and a photodiode with an optical band-pass filter 278 within a sensor chamber 271. Sensor chamber 271 is coupled to a signal processing electronics and metering valve control arrangement 282 which is also coupled to a metering valve 272. Sensor chamber 271 is coupled between the inlet valve 268 and metering valve 272. A by-pass line 270 also couples the inlet valve 268 and metering valve 272. A third line 274 couples the metering valve 272 to the fuel/air feed system of the vehicle.

A signal is provided from the signal processing electronics and metering valve control arrangement 282 to LED 276 for illuminating the vapochromic sensor 280 via LED 276. A feedback signal is then provided from the photodiode 278 to the signal processing electronics and metering valve control arrangement 282 which indicates the color of vapochromic sensor 280 and hence the level of fuel vapors (VOCs) in carbon canister 262. In accordance with a preset limit in the signal processing electronics and metering valve control arrangement 282, when the fuel vapor level within the carbon canister 262 exceeds a predetermined threshold, metering valve 272 is opened by the signal processing electronics and metering valve control arrangement for allowing fuel vapor to pass via the third line 274 to the vehicle's air/fuel feed system. In this manner, fuel vapors may be efficiently used in combination with liquid fuel provided to the vehicle's air/fuel feed system to fuel the vehicle's internal combustion engine. Clean air inlet 269 allows clean air to be routed to the vapochromic sensor 280 via inlet valve 268 for purging the sensor, while the sensor bypass line 270 permits fuel vapor to be routed around the vapochromic sensor 280 during purging.

Figure 11:
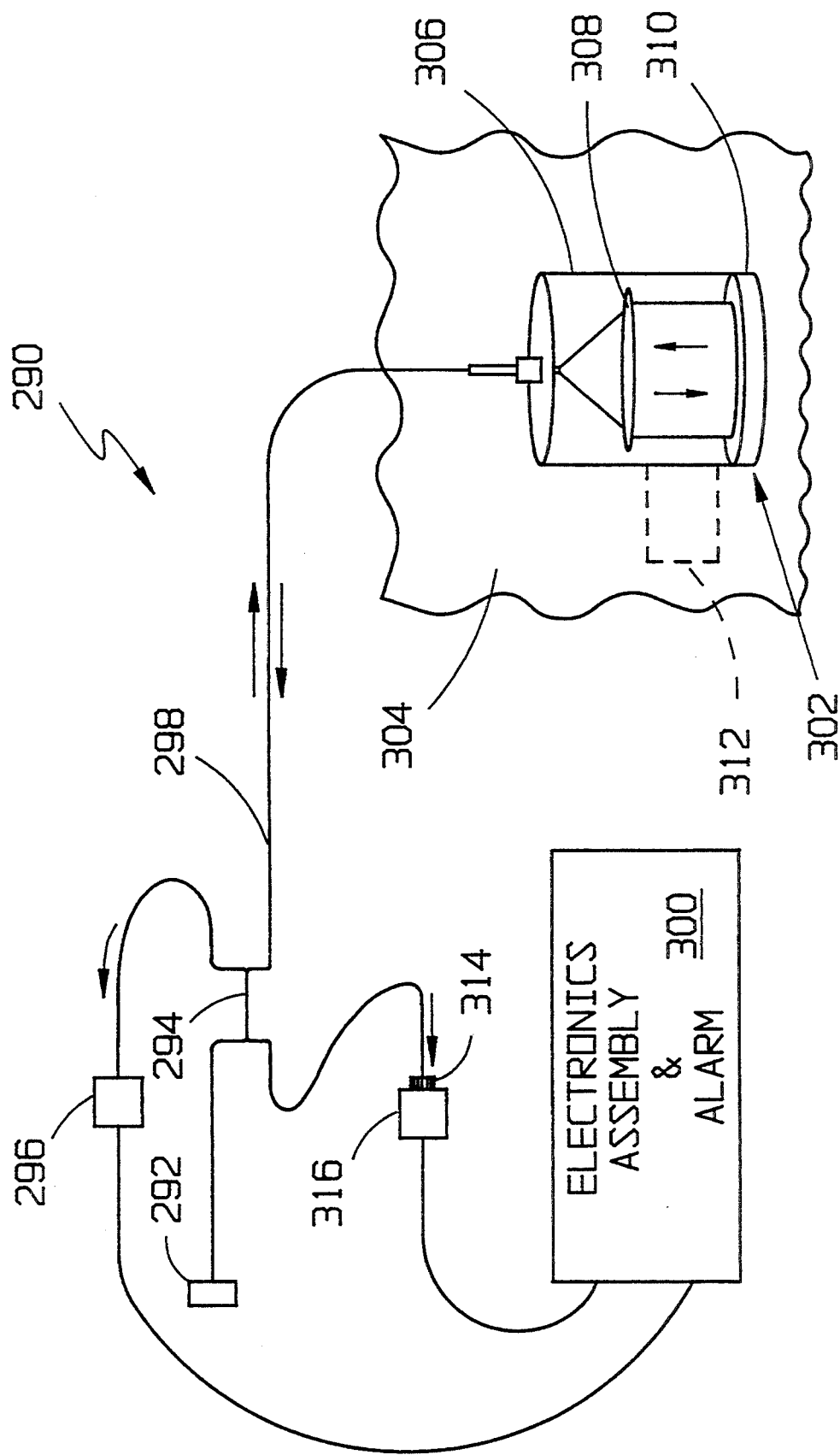
FIG. 11 is a simplified schematic diagram of a VOC colorimetric sensor for aqueous sensing in accordance with another embodiment of the present invention.

Referring to FIG. 11, there is shown another embodiment of a VOC colorimetric sensor 290 for aqueous VOC sensing. As in the previously described embodiments, VOC colorimetric sensor 290 includes a light source 292, a fiber optic beam-splitter 294, and a reference photodetector 296 for providing a reference input to an electronics assembly and alarm system 300. Light source 292 also provides a light signal to an aqueous sensor 302 via fiber optic beam-splitter 294 and an optical fiber 298. Aqueous sensor 302 includes a housing 306 within which is disposed a collimating lens 308 for directing the light beam onto a vapochromic sensing element 310. Collimating lens 308 also receives the light reflected from the vapochromic sensing element 310 and focuses it on the end of optical fiber 298 for providing a return light signal via the fiber optic beam-splitter 294 to the combination of an optical band-pass filter 314 and a detect photodetector 316. The detected optical signal is provided from photodetector 316 to the electronics assembly and alarm system 300 for comparison with the reference input for providing an alarm indication when the VOC level detected at the vapochromic sensing element 310 exceeds a predetermined threshold. Aqueous sensor 302 is submerged in water 304 and may include a sampling pump 312 shown in the figure in dotted-line form. Sampling pump 312 provides a continuous, uniform flow of water through the vapochromic sensing element 310 within housing 306. As shown in the figure, housing 306 is provided with apertures to allow for the free flow of water into and out of the housing. It has been found that a cross flow through housing 306 produced by sampling pump 312 results in fewer air bubbles within the housing and improved VOC aqueous matrix detection.

Figure 12:
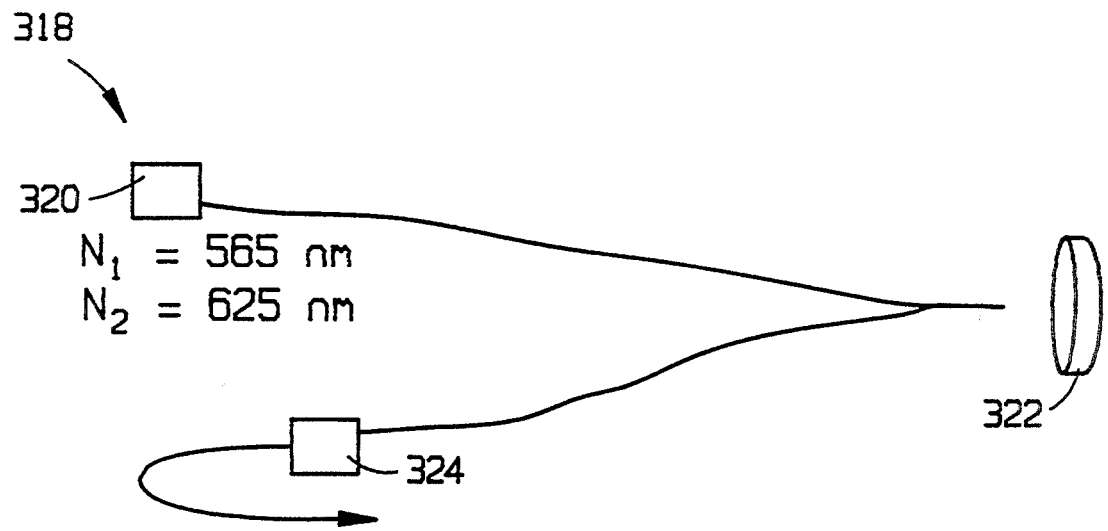
FIG. 12 is a simplified combined schematic and block diagram of yet another VOC detector arrangement in accordance with the principles of the present invention.
Figure 14:
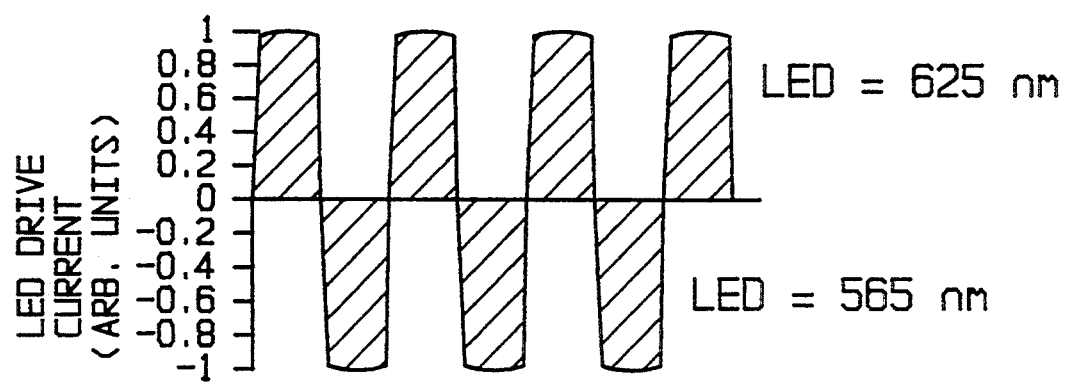
FIG. 14 is a graphic illustration of the LED drive current provided to the bi-color LED in the VOC detector arrangement of FIG. 12.
Figure 13:
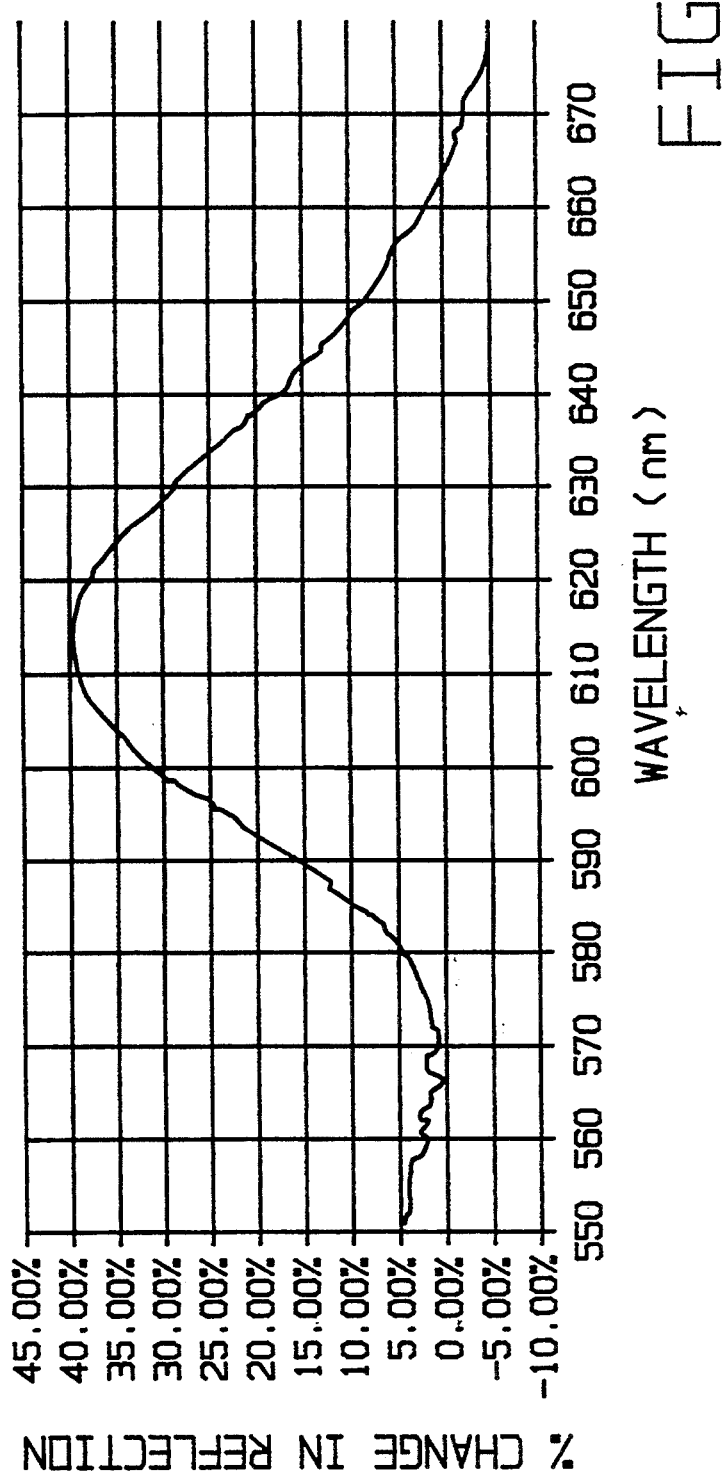
FIG. 13 is a graphic illustration of the percent of change of a light signal reflected from a VOC sensor over a bandwidth of from 550–670 nm.

Referring to FIG. 12, there is shown a simplified schematic and block diagram of a VOC detector arrangement 318 in accordance with another embodiment of the present invention. VOC detector arrangement 318 includes a light emitting bi-color LED 320 for directing light onto a vapochromic sensing element 322. Light reflected from the vapochromic sensing element 322 is provided to a detector 324 as in the previously described embodiments. The drive current to the hi-color LED 320 is adjusted so that its optical output alternates between 565 and 625 nm as shown graphically in FIG. 14. The reflected signal from the vapochromic sensing element 322 is stable for both wavelengths in an ambient state. The reflected signal at 625 nm will change up to approximately 40% in the presence of VOCs, whereas the reflected signal at 565 nm will not change appreciably in the presence of VOCs as shown graphically in FIG. 13. Gated detection electronics in detector 324 is synchronized with the LED drive current to monitor and detect small changes in the reflected signals at both wavelengths.

There has thus been shown various embodiments of a volatile organic compound (VOC) sensing device which employs vapochromic materials in the form of inorganic double complex salts which change color reversibly when exposed to VOC vapors. The various embodiments disclosed herein are particularly adapted for VOC vapor detection, VOC aqueous matrix detection and selective VOC vapor detection. The vapochromic sensor is used in combination with various fiber optic arrangements to provide a calibrated qualitative and/or quantitative indication of the presence of VOCs. The various embodiments disclosed herein include a ground probe sensor, a wristband sensor, a periodic sampling monitor, a soil/water penetrometer, and an evaporative purge sensor, and various vacuum-based sensors which are particularly adapted for reversible/reusable detection, remote detection, continuous monitoring, or rapid screening of environmental remediation and waste management sites.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

The embodiments of the invention in which an exclusive property or privilege is claimed are defined as follows:

1. Apparatus for detecting a volatile organic compound (VOC) comprising:
 a vapochromic sensor responsive to the presence of the VOC, wherein said vapochromic sensor undergoes a color change when in contact with the VOC;
 a sensor chamber containing said vapochromic sensor;
 a light source, a first light carrying optical fiber having at least three ends, a first end coupled, to said sensor chamber for providing a reference light beam and for directing said reference light beam into said sensor chamber and onto said vapochromic sensor;
 a second light carrying optical fiber having a first end coupled, to said sensor chamber, wherein said first end of said second light carrying optical fiber is responsive to light reflected from said vapochromic sensor;
 a means for displacing a medium containing the VOC through said sensor chamber; and
 detection means coupled to a second end of said first light carrying optical fiber and to a second end of said second light carrying optical fiber for comparing said reference light beam and the light reflected from said vapochromic sensor for determining a color change in said vapochromic sensor arising from the presence of the VOC, wherein a third end of said first light carrying optical fiber is coupled to said light source.

2. The apparatus of claim 1 wherein said means for displacing said medium includes a vacuum pump for drawing air through said sensor chamber.

3. The apparatus of claim 1 wherein said means for displacing said medium includes a pump for drawing water through said sensor chamber.

4. The apparatus of claim 1 further comprising a fiber optic beam-splitter coupling said first light carrying optical fiber to said sensor chamber and to said detector means.

5. The apparatus of claim 4 further including a band-pass filter coupled to the first end of said second light carrying optical fiber for producing a large signal representing a color change in said vapochromic sensor arising from the presence of the VOC.

6. The apparatus of claim 1 wherein said first and second light carrying optical fiber further comprises a common optical fiber coupled to said sensor chamber for carrying said reference light beam and light reflected from said vapochromic sensor.

7. The apparatus of claim 1 wherein said detection means includes an audio or visual alarm.

8. The apparatus of claim 1 wherein said sensor chamber includes a VOC selective member for allowing the VOC to enter said sensor chamber while preventing other materials from contacting said vapochromic sensor.

9. The apparatus of claim 1 further comprising a collimating lens disposed in said sensor chamber for receiving and collimating said reference beam and directing said colliminated reference light beam onto said vapochromic sensor and for focusing light reflected from said vapochromic sensor onto the first end of said second light carrying optical fiber.

10. The apparatus of claim 1 wherein said sensor chamber is in a soil or water penetrometer.

11. The apparatus of claim 1 further comprising means for adjusting spacing between the first end of said first light carrying optical fiber and said vapochromic sensor for increasing the amount of light incident upon said vapochromic sensor.

12. Apparatus for detecting a volatile organic compound (VOC) in a fuel tank of a vehicle and providing fuel vapors to an air/fuel system of said vehicle comprising:
- a vapochromic sensor responsive to the presence of the VOC, wherein said vapochromic sensor undergoes a color change when in contact with the VOC;
- an evaporative purge sensor including a sensor chamber containing said vapochromic sensor for use in providing the fuel vapors in the vehicle's fuel tank to the vehicles's air/fuel feed system;
- a clean air inlet coupled to the evaporative purge sensor for purging said evaporative purge sensor;
- a light source, and a first light carrying optical fiber, coupling said light source to said evaporative purge sensor for providing a reference light beam and for directing said reference light beam into said evaporative purge sensor and onto said vapochromic sensor;
- a light detector, and a second light carrying optical fiber, coupling said light detector to said evaporative purge sensor, said light detector is responsive to light reflected from said vapochromic sensor; and
- detection means electronically coupled to said light source and said light detector for comparing said reference light beam and the light reflected from said vapochromic sensor for determining a color change in said vapochromic sensor arising from the presence of the VOC and providing the fuel vapors to the vehicle's air/fuel system.

13. An evaporative purge sensor for use in monitoring fuel vapors in a fuel tank of a vehicle and providing said fuel vapors to an air/fuel system of said vehicle, said evaporative purge sensor comprising:
- a carbon canister including a carbon filter for absorbing and removing said fuel vapors from the fuel tank, wherein said carbon canister also contains fuel vapors when the carbon filter in said canister becomes saturated with fuel;
- an optical sensor including a vapochromic material responsive to the presence of fuel vapors, wherein said vapochromic material undergoes a color change when in contact with fuel vapors;
- valve means for coupling said optical sensor to said carbon canister and to the vehicle's air/fuel system;
- purge means coupled to said valve means for purging said optical sensor, and;
- control means coupled to said valve means and to said optical sensor for comparing the amount of fuel vapors in said optical sensor with a predetermined level of fuel vapors and for opening said valve, means and providing the fuel vapors to the vehicle's air/fuel system when said predetermined level is exceeded.

14. The apparatus of claim 13 wherein the purge means further comprises a clean air inlet coupled to said valve means 15. The apparatus of claim 14 wherein the purge means further comprises a bypass line coupled to said valve means permitting fuel vapors to be routed around said optical sensor during purging.

* * * * *